US010609938B2

(12) United States Patent
Hristov

(10) Patent No.: US 10,609,938 B2
(45) Date of Patent: Apr. 7, 2020

(54) FEED COMPOSITION FOR REDUCING AMMONIA PRODUCED IN ANIMAL AGRICULTURE AND METHODS FOR MAKING AND USING THE FEED COMPOSITION

(71) Applicant: Nutes Oy, Helsinki (FI)

(72) Inventor: Alexander Nikolov Hristov, State College, PA (US)

(73) Assignee: Nutes Oy, Helsinki (FI)

( * ) Notice: Subject to any disclaimer, the term of this patent is extended or adjusted under 35 U.S.C. 154(b) by 171 days.

(21) Appl. No.: 15/327,900

(22) PCT Filed: Jul. 21, 2014

(86) PCT No.: PCT/US2014/047403
§ 371 (c)(1),
(2) Date: Jan. 20, 2017

(87) PCT Pub. No.: WO2016/014019
PCT Pub. Date: Jan. 28, 2016

(65) Prior Publication Data
US 2017/0231253 A1    Aug. 17, 2017

(51) Int. Cl.
| *A23K 50/10* | (2016.01) |
| *A23K 20/174* | (2016.01) |
| *A23K 20/158* | (2016.01) |
| *A23K 40/35* | (2016.01) |
| *A23K 20/147* | (2016.01) |
| *A23K 20/142* | (2016.01) |
| *A23K 20/163* | (2016.01) |
| *A23K 10/20* | (2016.01) |
| *A23K 10/37* | (2016.01) |
| *A23K 10/30* | (2016.01) |
| *A23K 10/38* | (2016.01) |
| *A23K 20/22* | (2016.01) |
| *A23K 20/24* | (2016.01) |
| *A23K 20/26* | (2016.01) |
| *A61K 31/20* | (2006.01) |
| *A61K 31/66* | (2006.01) |

(52) U.S. Cl.
CPC ............ *A23K 50/10* (2016.05); *A23K 10/20* (2016.05); *A23K 10/30* (2016.05); *A23K 10/37* (2016.05); *A23K 10/38* (2016.05); *A23K 20/142* (2016.05); *A23K 20/147* (2016.05); *A23K 20/158* (2016.05); *A23K 20/163* (2016.05); *A23K 20/174* (2016.05); *A23K 20/22* (2016.05); *A23K 20/24* (2016.05); *A23K 20/26* (2016.05); *A23K 40/35* (2016.05); *A61K 31/20* (2013.01); *A61K 31/66* (2013.01); *Y02P 60/873* (2015.11); *Y02P 60/877* (2015.11)

(58) Field of Classification Search
None
See application file for complete search history.

(56) References Cited

U.S. PATENT DOCUMENTS

| 3,644,642 A | | 2/1972 | Wilson et al. |
| RE35,964 E | * | 11/1998 | Wellons ............... A23K 20/158 |
| | | | 426/2 |
| 2002/0136778 A1 | * | 9/2002 | Claycamp .............. A61K 35/20 |
| | | | 424/581 |
| 2004/0154988 A1 | * | 8/2004 | Sheets, Sr. .............. C02F 11/14 |
| | | | 210/718 |
| 2007/0212384 A1 | | 9/2007 | Ledgard |
| 2008/0014323 A1 | | 1/2008 | Vazquez-Anon et al. |
| 2009/0110800 A1 | | 4/2009 | Wilkes |
| 2016/0192678 A1 | * | 7/2016 | Wan ..................... A23K 20/158 |
| | | | 426/2 |
| 2016/0205969 A1 | * | 7/2016 | Wan ..................... A23K 20/158 |
| 2016/0255864 A1 | * | 9/2016 | Wan ..................... A23K 40/10 |
| 2016/0255865 A1 | * | 9/2016 | Wan ..................... A23K 20/158 |
| 2017/0223988 A1 | * | 8/2017 | Holma .................. A23K 50/10 |

FOREIGN PATENT DOCUMENTS

| CN | 101564118 A | * | 10/2009 |
| CN | 100586300 C | | 2/2010 |
| EP | 2676551 A1 | | 12/2013 |
| WO | 2013071344 A1 | | 5/2013 |

OTHER PUBLICATIONS

Warntjes et al, "Effects of feeding supplemental palmitic acid (C16:0) on performance and milk fatty acid profile of lactating dairy cows under summer heat", Animal Feed Science and Technology, 140, 241-257, 2008 (Year: 2008).*
English translation of CN 101564118 A obtained from EPO and Google, obtained on Jun. 21, 2018 (Year: 2018).*
Farid, webpage at www.nifa.org [retrieved on Aug. 21, 2018]. Published at least as early as Apr. 30, 2011. Retrieved from the Internet: <URL: https://www.nifa.org.pk/FSDMilkThistle.htm>. (Year: 2011).*
Mahernia, "Urease Inhibitory Activities of some Commonly Consumed Herbal Medicines", Iranian Journal of Pharmaceutical Research, 14 (3): 943-947, 2015 (Year: 2015).*
Oliveira, "In Vitro Antimicrobial and Modulatory Activity of the Natural Products Silymarin and Silibinin", BioMed Research International, vol. 2015, Article ID 292797, 7 pages (Year: 2015).*
International Search Report and Written Opinion for International Application No. PCT/US2014/047403 dated Jan. 22, 2015, pp. 10.
Ludden et al., Influence of the novel urease inhibitor N-(n-butyl) thiophosphoric triamide on ruminant nitrogen metabolism: II. Ruminal nitrogen metabolism, diet digestibility, and nitrogen balance in lambs (Jan. 2000), J Anim Sci., 78(1) pp. 188-198.
Suksombat, Improving the productivity of lactating dairy cows through supplementation, International Dairy Topics (2009), 8(1) pp. 7-11.

* cited by examiner

*Primary Examiner* — David J Blanchard
*Assistant Examiner* — John P Nguyen
(74) *Attorney, Agent, or Firm* — Christensen O'Connor Johnson Kindness PLLC

(57) ABSTRACT

A feed composition for ruminants may include feed particles that contain a saturated fatty acid component as well as a urease inhibitor such that ingestion of the feed by lactating ruminants may provide for an increase in the amount of milk produced by the ruminant and/or an increase in the fat content of the milk produced, and a decrease in ammonia production from breakdown of urea.

17 Claims, 2 Drawing Sheets

- nutritional component
- fatty acid component
- urease inhibitor

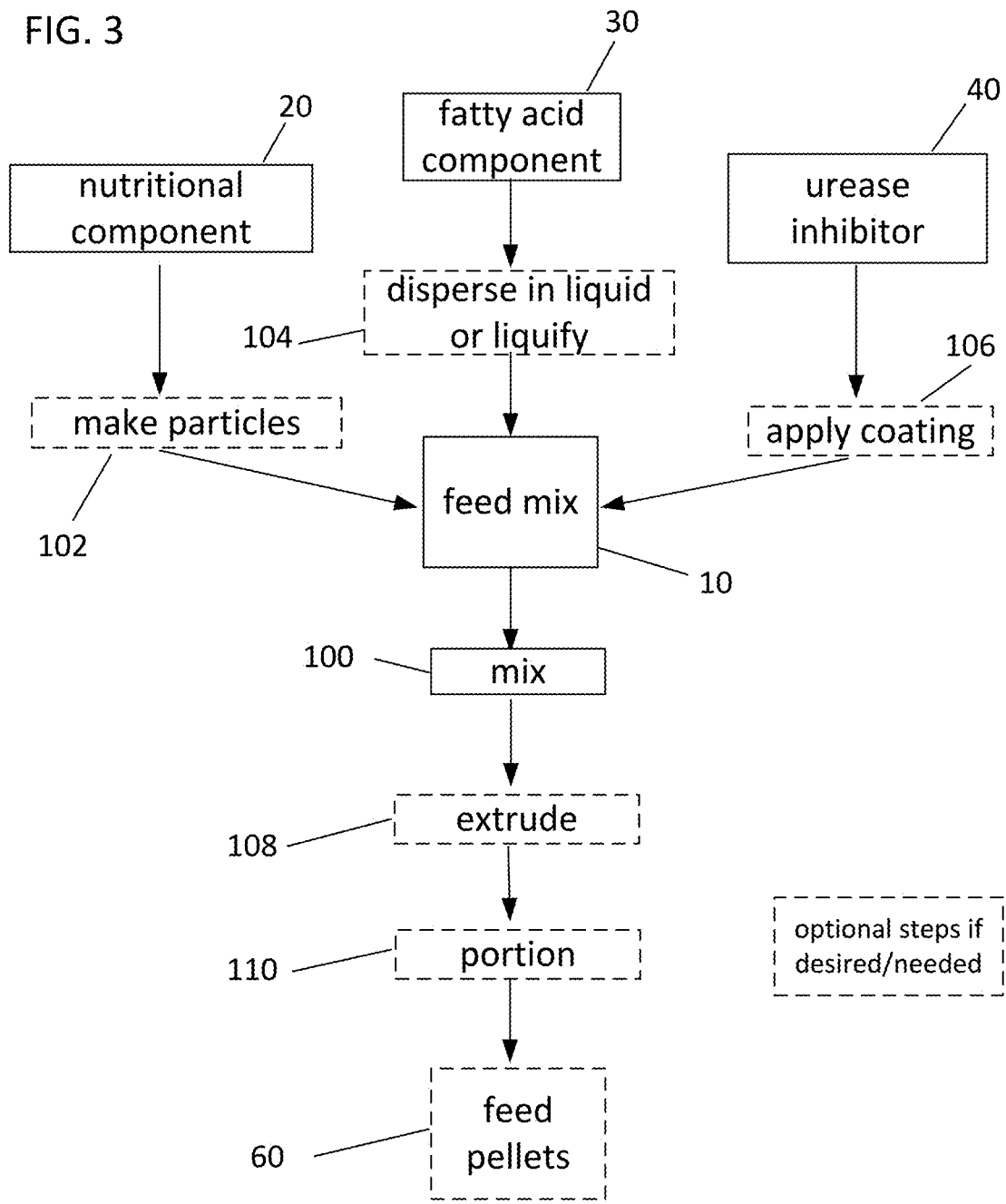

FEED COMPOSITION FOR REDUCING AMMONIA PRODUCED IN ANIMAL AGRICULTURE AND METHODS FOR MAKING AND USING THE FEED COMPOSITION

CROSS-REFERENCE TO RELATED APPLICATION

The present application is a U.S. National Stage filing under 35 U.S.C. § 371 of International Patent Application No. PCT/US2014/047403, filed on Jul. 21, 2014, and entitled "FEED COMPOSITION FOR REDUCING AMMONIA PRODUCED IN ANIMAL," which is incorporated herein by reference in its entirety.

BACKGROUND

In animal agriculture, increasing milk production and improving milk quality of the milk produced have been primary goals when feeding lactating dairy animals, such as dairy cows. Depending on the animal, the feed components may vary considerably. For example, ruminants are able to digest fibrous plant based foods, or roughage, that are indigestible to non-ruminants. Ruminants may include lactating animals such as, for example, cattle, goats, sheep, and dairy cows. Illustrative types of roughages include hay, grass silage, corn silage, straw and pasture, as well as various whole grain/leguminous silages and other fodders.

For efficient milk production, ruminants may also be given, in addition to roughage, a feed concentrate that may include energy components (that is, carbohydrates and fats), protein components, minerals, micronutrients, and vitamins. Some examples of common feed items include grain feeds (such as corn, oats, barley, and wheat), vegetable oilseed crushes or meal (rapeseed), and soybeans. A large variety of byproducts from food industries may also be used.

By means of microbes within the rumen digestive system, most of the energy and nutrients needed by the ruminant are obtained from the feed. Nitrogen containing materials, which may be natural proteins or non-protein sources such as urea, may be broken down and converted into amino acids and proteins by the microorganisms of the rumen. Both urea and natural protein are broken down by the microorganisms in the rumen to ammonia and carbon fragments, and are thereafter reconstituted, together with carbohydrate degradation products, to form amino acids. The amino acids may be used to build protein that may subsequently be used by the host animal. The carbohydrate degradation process provides energy for the amino acid reconstitution process.

However, urea may not be efficiently used by the host animal. In the rumen, via urease, urea may be converted into ammonia at a very rapid rate, generally, at a rate in excess of the rate at which the urea can be converted into useful products by the microorganisms. Any leftover ammonia may be converted back into urea to be expelled with urine, or may accumulate to toxic levels in the animal. Urea expelled in the urine may be converted to ammonia on the ground by contact with urease often found in the feces or soil. In the air, ammonia can combine with other compounds to form ammonium nitrate and ammonium sulfate, which are fine particulates. These particulates are of concern for human health and are regulated under the Clean Air Act. Therefore, regulating the production of ammonia from urea to provide an optimal concentration of ammonia in the digestive system and minimizing the release of ammonia from animal feeding operations is desirable.

SUMMARY

To provide for an increase in the amount of milk produced by a ruminant, and/or an increase in the fat content of the milk produced, while also minimizing generation of ammonia by ruminants, the ruminant may be provided with a feed composition that includes feed particles containing a saturated fatty acid as well as a urease inhibitor. The urease inhibitors may be encapsulated or coated to protect the urease inhibitors from rumen microorganisms.

In an embodiment, a feed composition for lactating ruminants includes a nutritional component, a saturated fatty acid component, and at least one urease inhibitor.

In an embodiment, a method of producing a feed for lactating ruminants includes combining a nutritional component, at least one urease inhibitor, and a saturated fatty acid component.

In an embodiment, a method is provided for decreasing ammonia formation in ruminants being farmed for milk production while increasing at least one of an amount of milk produced by a lactating ruminant and a milk fat content in the milk produced by the lactating ruminant. The method includes feeding a lactating ruminant an animal feed that includes a nutritional component, at least one urease inhibitor, and a saturated fatty acid component.

BRIEF DESCRIPTION OF THE FIGURES

FIG. 3 depicts a representative method for producing a feed particle containing a urease inhibitor according to an embodiment.

DETAILED DESCRIPTION

Figure 1:
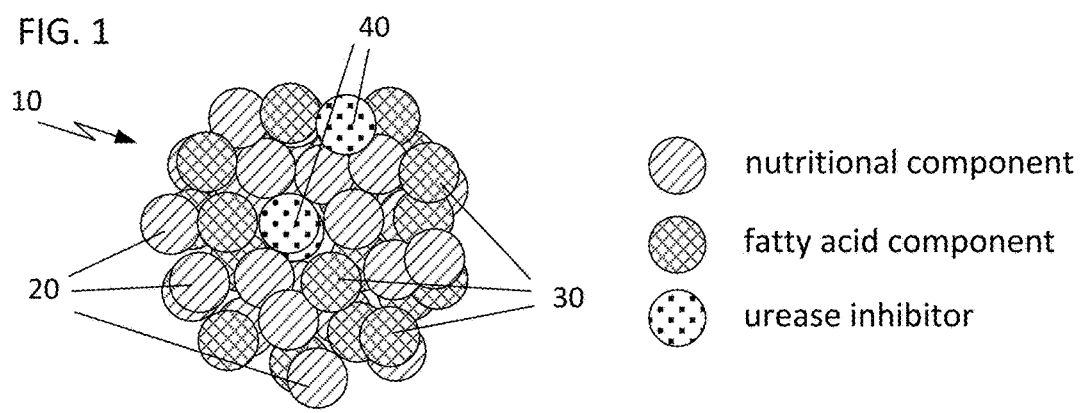
FIG. 1 depicts a representation of a feed particle that includes a urease inhibitor according to an embodiment.

With respect to the description presented herein, a "ruminant" is a class of mammal with a multiple chamber stomach that gives the animal an ability to digest cellulose-based food by softening it within the first chamber (rumen) of the stomach and regurgitating the semi-digested mass. The regurgitate, known as cud, is then chewed again by the ruminant. Specific examples of ruminants include, but are not limited to, cattle, bison, buffaloes, yaks, camels, llamas, giraffes, deer, pronghorns, antelopes, sheep, and goats. The milk produced by ruminants is widely used in a variety of dairy-based products. Dairy cows are of considerable commercial significance for the production of milk and processed dairy products such as, for example, yogurt, cheese, whey, and ice cream.

The formation of milk in the mammary gland is a complex enzymatic process regulated by hormones, requiring a significant amount of adenosine triphosphate (ATP) energy at the cell level, as well as suitable starting materials and enzymes. The main components of milk, lactose, protein, and fat, are synthesized in the cells of the udder.

Microbes in the rumen ferment carbohydrates of the feed to acetic acid, butyric acid and propionic acid, with propionic acid generally being the most important precursor of glucose. Glucose availability in the mammary gland and the availability of some amino acids have typically been regarded as the main limiting factors in milk production. These acids may be transported to the liver where they are converted to useful nutrients. Acetate may be consumed in the liver to produce energy and may also be converted to longer fatty acids. These fatty acids may function as precursors to milk fat. Part of the acetate may be transferred with the blood circulation to the mammary gland, where the acetate may be used for the synthesis of fatty acids generally having sixteen or fewer carbon atoms. Butyric acid may also be used as a precursor of milk fat.

Cell energy in the form of ATP is generated in the mitochondria. Cells of the mammary gland contain dozens of mitochondria. An intermediate product in ATP formation is called active acetic acid (acetyl-CoA). Acetyl-CoA is generally obtained from carbohydrates and fats. However, in situations where energy is lacking, acetyl-CoA may also be obtained from carbon chains of proteins, a process which is not economical. A ruminant does not use much glucose to produce acetyl-CoA. Instead, the main source of acetyl-CoA in ruminants, in addition to the acetic acid formed in the rumen, is acetate that is derived from the β-oxidation of fatty acids.

It has been determined that saturated fatty acids, when included in feed, may be surprisingly suitable for producing acetic acid and also acetyl-CoA. Saturated fatty acids, which may include but are not limited to, palmitic acid, stearic acid and myristic acid, may therefore be an important source of energy. For example, if the eight acetyl-CoAs produced from palmitic acid are used for complete oxidation in the citric acid cycle, 129 ATP molecules may be obtained from one palmitic acid molecule.

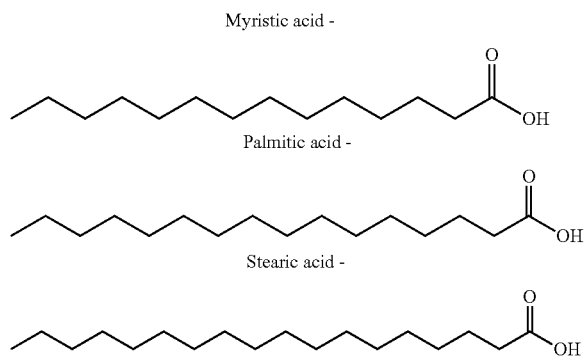

The amino acids needed for the synthesis of milk protein may be partly obtained from the blood. Non-essential amino acids may be synthesized in the mammary gland using the carbon C2 chain of acetate. However, this process also requires ATP energy. Approximately 30 mmol ATP/1 g protein is needed in this protein synthesis. The energy needed for the synthesis of milk fat varies depending on how the milk fat is formed. In some cases, a portion of the fatty acids may be obtained in de novo synthesis in the mammary gland or by conversion in the rumen or in the liver. Alternately or additionally, a portion of the fatty acids may be obtained via the digestive tract from the feed.

When fatty acids are synthesized in the udder (that is, de novo synthesis), about 27 mmol ATP per gram of fat is required. Therefore, more energy may be saved for other purposes if more milk fat components are obtained as fatty acids from blood circulation. Short and middle-chain fatty acids are obtained only via de novo synthesis, and the long-chain fatty acids (C18 and longer) are obtained only from blood circulation. Of the milk fatty acids, essentially only palmitic acid can be produced in both ways.

For the production of protein, it is generally believed that nitrogen-containing material fed to the animal is converted into protein by the complex microorganisms of the rumen. The nitrogen-containing material is digested, assimilated, and converted to organismal protein by the host animal. The nitrogen-containing material may be a protein or a non-protein nitrogen source, such as urea. Urea is attractive as a nitrogen-containing supplement in feeding ruminants because it represents a concentrated and low-cost source of nitrogen.

Urea may often be fed to ruminants for the purpose of supplementing natural protein in feeds such as hay and grains. Both urea and natural protein are broken down by the complex microorganisms in the rumen to ammonia and carbon fragments. Thereafter, the ammonia and carbon fragments may be reconstituted, together with carbohydrate degradation products, to form amino acids. At least some of the amino acids may be used to build protein for use by the host animal. The carbohydrate degradation process provides energy for the amino acid reconstitution process.

However, the host animal may not efficiently use urea because it may be converted to ammonia faster than the rate at which ammonia may be converted to amino acids by microorganisms in the rumen. If ammonia becomes available before the carbohydrates have fermented, that is, before energy is available to convert the ammonia to amino acids, the ammonia may be lost in the animal excreta, or, if not gotten rid of, may cause a condition of toxicity to develop. Excess ammonia may also be converted back into urea which may be expelled with urine. Urea expelled in urine may be converted to ammonia on the ground by contact with urease found in animal feces and soil. In the air, ammonia may combine with other compounds to form ammonium nitrate and ammonium sulfate, which are fine particulates that are of concern for human health.

It has been surprisingly determined that a certain type of nutriment for lactating ruminants may control ammonia production and utilization while efficiently increasing the proportion of milk fat derived from the feed. With such a feed, the mammary gland may function primarily on the synthesis of protein and lactose. Milk production may be increased and release of ammonia into the surrounding environment may be controlled. In an embodiment represented in FIG. 1, a feed 10 for lactating ruminants may include a nutritional component 20, a saturated fatty acid component 30, and a urease inhibitor 40.

During the hydrolysis of urea, urea is converted in the presence of water and the enzyme urease to produce ammonium carbonate.

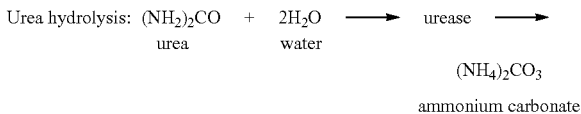

Ammonium carbonate then reacts with hydrogen ions to produce ammonium, carbon dioxide, and water.

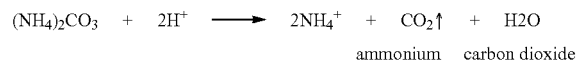

The ammonium produced may then form ammonia.

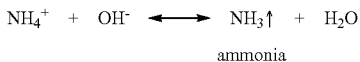

With the inclusion of a urease inhibitor 30 in the feed 10, the initial reaction sequence above may be slowed down or delayed by inhibiting at least some of the urease from acting upon the urea, thereby resulting in a slower or delayed production of ammonia that may allow for essentially all of the ammonia to be processed for producing amino acids, minimizing animal toxicity and release of ammonia into the atmosphere.

In an embodiment, the feed composition may include up to about 10 weight percent urease inhibitor. As examples, the weight percent urease inhibitor concentration in the feed may be about 10%, about 9%, about 8%, about 7%, about 6%, about 5%, about 4%, about 3%, about 2%, about 1%, or any value or range between any two of the listed values (including endpoints).

Some general types of urease inhibitors may include, but are not limited to sulphydryl reagents, hydroxamates, urea analogues, or any combination thereof. In embodiments, the urease inhibitor may be selected from N-(n-butyl) thiophosphoric triamide, N-(n-butyl) phosphoric triamide, thiophoshoryl triamide, phenyl phosphorodiamidate, cyclohexyl thiophosphoric triamide, cyclohexyl phosphoric triamide, phosphoric triamide, hydroquinone, P-benzoquinone, hexaamidocyclotriphosphazene, thiophyridines, thiophyrimidines, thiophyridine-noxides, NN-dihalo-2-imidazolidinone, N-halo-2-oxazolidinone, acetohydroxamic acid, or any combination thereof. In an embodiment, a feed for lactating ruminants may include a nutritional component, a saturated fatty acid component, and N-(n-butyl) thiophosphoric triamide as the urease inhibitor.

Figure 2:
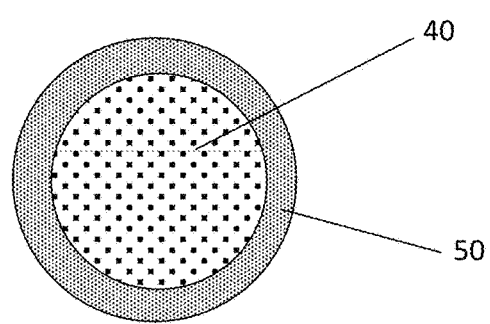
FIG. 2 depicts a representation of a coated urease inhibitor according to an embodiment.

In an embodiment as represented in FIG. 2, the urease inhibitor 40 may be coated with a coating material 50 that may, for example, protect the urease inhibitor from rumen microorganisms, delay the exposure of the urease inhibitor for delayed function in the digestive tract, and/or release the urease inhibitor after passage through the animal, for example, in manure. Some types of coatings 50 that may be applied to the urease inhibitor 40 may include, but are not limited to chitosan, a lipid/protein mixture, pH-dependent polymers, commercial lipid formulations, or any combination thereof. A few examples of commercial lipid formulations may include Balchem's SHURE technology (Balchem Corp., New Hampton, N.Y.) and Innovad's NOVILYS (Innovad sa/nv, Essen, Belgium). In an embodiment, a feed may include some urease inhibitor that is uncoated for essentially immediate use in the digestive tract, and some urease inhibitor that is coated for delayed use. Alternatively, a feed may include some urease inhibitor that is uncoated for essentially immediate use in the digestive tract, as well as additional urease inhibitor factions that have different coatings to provide alternate periods of delayed use, so that the function of the urease inhibitor in the digestive tract may be drawn out over an extended period of time.

In an embodiment, some of the urease inhibitor may be configured to pass completely though the digestive tract so that it is expelled in the feces, whereby the urease inhibitor may be available for inhibiting action of urease in the feces with urine urea to provide for a decreased production of ammonia outside of the animal. For this purpose, the urease inhibitor may be provided with a coating that is sufficient to protect the urease inhibitor from digestion at least for a period of time sufficient for passage through the digestive tract.

The saturated fatty acid component 30 of the feed 10 may provide for the transfer of the fatty acids, via the digestive tract, into the blood circulation for providing saturated fatty acids to the udder. The saturated fatty acid component 30 may be at least about 3 weight percent of the feed 10. In an alternative embodiment, the saturated fatty acid component 30 may be at least about 10 weight percent of the feed 10.

In an embodiment, the saturated fatty acid component may include a saturated fatty acid component that may have a melting temperature of at least about 60° C. The saturated fatty acid component may include at least one saturated fatty acid moiety having a melting temperature of about 60° C. to about 80° C. In various embodiments, the saturated fatty acid component may have a melting temperature of about 60° C., about 62° C., about 64° C., about 66° C., about 68° C., about 70° C., about 72° C., about 74° C., about 76° C., about 78° C., about 80° C., or any value or range between any two of the listed values (including endpoints).

In an embodiment, the saturated fatty acid component may include at least one moiety of palmitic acid. As an example, the saturated fatty acid component may include at least about 70% of the at least one moiety of palmitic acid. In various embodiments, the weight percent of the at least one moiety of palmitic acid in the saturated fatty acid component may be about 70%, about 75%, about 80%, about 85%, about 90%, about 95%, about 100%, or any value or range between any two of the listed values (including endpoints).

Moieties of palmitic acid may include, but are not limited to, palmitic acid, palmitic acid derivatives, or any combination thereof. Some examples of palmitic acid derivatives may include, but are not limited to, palmitic acid esters, palmitic acid phosphonates, palmitic acid amides, palmitic acid salts, palmitic acid carbonates, palmitic acid carbamates, palmitic acid imides, palmitic acid anhydrides, or any combination thereof.

In an embodiment, the saturated fatty acid component may include free palmitic acid. In a further embodiment, the saturated fatty acid component may include at least about 70 weight percent of the free palmitic acid. In various embodiments, in which the saturated fatty acid component includes free palmitic acid, the weight percent of free palmitic acid in the saturated fatty acid component may be about 70%, about 75%, about 80%, about 85%, about 90%, about 95%, about 100%, or any value or range between any two of the listed values (including endpoints). In an embodiment, a feed for lactating ruminants may include a nutritional component, a urease inhibitor, and a saturated fatty acid component that may include at least about 90 weight percent free palmitic acid.

In an embodiment, the saturated fatty acid component may include at most about 30 weight percent free stearic acid. Stearic acid in greater amounts may hinder the milk production capacity of the mammary gland. In various embodiments, in which the saturated fatty acid component may include free stearic acid, the weight percent of free stearic acid in the saturated fatty acid component may be about 30%, about 25%, about 20%, about 15%, about 10%, about 5%, about 0%, or any value or range between any two of the listed values (including endpoints).

In various embodiments, in which the saturated fatty acid component may include essentially only free palmitic acid and free stearic acid, various ratios by weight of palmitic acid to stearic acid may include about 70:30, about 75:25, about 80:20, about 85:15, about 90:10, about 95:5, about 100:0, or any ratio or range between any two of the listed values (including endpoints).

The nutritional component 10, as represented in FIG. 1, may include one or more of carbohydrate sources, protein sources, non-protein nitrogen sources, amino acids or derivatives, vitamins, minerals, glycogenic precursors, and antioxidants. Feed compositions may also include auxiliary agents, which may include pelletizing agents, such as lignin sulphates and/or colloidal clay. In embodiments, the nutritional component may be a wood particle, a hay particle, a grain particle, a protein particle, a yeast particle, or any combination thereof.

Some examples of carbohydrate sources may include, but are not limited to, sugar beet pulps, sugar canes, wheat bran, oat hulls, grain hulls, soybean hulls, peanut hulls, wood, brewery byproduct, forages, roughages, sugars, starch, cellulose, hemicellulose, and grain sources, including wheat, corn, oats, sorghum, millet, and barley. These carbohydrates may be used independently or in combination. In embodiments, the carbohydrate content of the mixture may be about 0.1 wt % to about 50 wt %, about 5 wt % to about 40 wt %, about 5 wt % to about 35 wt %, or about 5 wt % to about 20 wt %. Specific examples of carbohydrate content include about 0.1 wt %, about 1 wt %, about 5 wt %, about 10 wt %, about 20 wt %, about 30 wt %, about 40 wt %, about 50 wt %, and ranges between any two of these values (including endpoints).

Some examples of protein sources may include, but are not limited to, soybean, canola (rapeseed), cottonseed, corn gluten meal, oilseed meals such as palm oil, animal by-product meals such as meat meal, poultry meal, blood meal, feather meal, and fish meal, plant by-product meals such as wheat middlings, soybean hulls, and corn by-products, and microbial protein such as torula yeast and brewer's yeast. These protein sources may be used independently or in combination. In various embodiments, the protein content of the feed may be about 0.1 wt % to about 55 wt %, about 5 wt % to about 45 wt %, or about 8 wt % to about 40 wt %. Specific examples of protein content include about 0.1 wt %, about 1 wt %, about 5 wt %, about 10 wt %, about 20 wt %, about 30 wt %, about 40 wt %, about 50 wt %, and ranges between any two of these values (including endpoints).

Some examples of non-protein nitrogen sources may include urea, ammonium acetate, ammonium bicarbonate, ammonium carbamate, ammonium lactate, ammonium formate, biuret, dicyanodiamide, glutamine, asparagine, glycine, oilseed meals such as soy meal, bean meal, rapeseed meal, sunflower meal, linseed meal, and grapeseed meal, as well as coconut meal and olive meal. These non-protein nitrogen sources may be used independently or in combination. In various embodiments, the non-protein nitrogen source content of the feed may be about 1 wt % to about 4 wt %. Specific examples of non-protein nitrogen source content include about 1 wt %, about 1.2 wt %, about 1.4 wt %, about 1.6 wt %, about 1.8 wt %, about 2 wt %, about 2.2 wt %, about 2.4 wt %, about 2.6 wt %, about 2.8 wt %, about 3 wt %, about 3.2 wt %, about 3.4 wt %, about 3.6 wt %, about 3.8 wt %, about 4 wt %, and ranges between any two of these values (including endpoints). In feed supplements, the non-protein nitrogen source content may be as much as 10 wt %. Specific examples of non-protein nitrogen source content in supplements include about 5 wt %, about 5.5 wt %, about 6 wt %, about 6.5 wt %, about 7 wt %, about 7.5 wt %, about 8 wt %, about 8.5 wt %, about 9 wt %, about 9.5 wt %, about 10 wt %, and ranges between any two of these values (including endpoints).

Some examples of amino acid sources, may include, but are not limited to, essential amino acids, nonessential amino acids, common amino acids, uncommon amino acids, and derivatives of any of the amino acids. Additional examples may include, but are not limited to, leucine, lysine, histidine, valine, arginine, threonine, isoleucine, phenylalanine, methionine, tryptophan, and their protected forms and derivatives. These amino acid sources may be used independently or in combination.

Some examples of vitamins, may include, but are not limited to, vitamin A, vitamin D, vitamin E, vitamin B1, vitamin B2, pantothenic acid, niacin, biotin, choline, carnitine, or any combination thereof.

Some examples of minerals may include, but are not limited to, ions of calcium, sodium, magnesium, phosphorous, and potassium and trace elements manganese, zinc, selenium, copper, iodine, iron, cobalt and molybdenum. These minerals and trace elements may be provided using any of a number of mineral sources. In general, any GRAS (generally recognized as safe) mineral source may be used which provides a bioavailable mineral. Table 1 below provides some examples of suitable mineral sources.

TABLE 1

| GRAS Mineral Sources | | | |
|---|---|---|---|
| Calcium Acetate | Calcium Carbonate | Calcium Chloride | Calcium Gluconate |
| Calcium Hydroxide | Calcium Iodate | Calcium Iodobehenate | Calcium Oxide |
| Calcium Sulfate (anhydrous or dihydrate) | Cobalt Acetate | Cobalt Carbonate | Cobalt Chloride |
| Cobalt Oxide | Cobalt Sulfate | Dicalcium Phosphate | Magnesium Acetate |
| Magnesium Carbonate | Magnesium Oxide | Magnesium Sulfate | Manganese Carbonate |
| Manganese Chloride | Manganese Citrate (soluble) | Manganese Gluconate | Manganese Orthophosphate |
| Manganese Oxide | Manganese Phosphate (dibasic) | Manganese Sulfate | Monocalcium Phosphate |
| Monosodium Phosphate | Potassium Acetate | Potassium Bicarbonate | Potassium Carbonate |
| Potassium chloride | Potassium Iodate | Potassium Iodide | Potassium Sulfate |
| Sodium Acetate | Sodium Chloride | Sodium Bicarbonate | Disodium Phosphate |
| Iron Ammonium Citrate | Iron Carbonate | Iron Chloride | Iron Gluconate |
| Iron Oxide | Iron Phosphate | Iron Pyrophosphate | Iron Sulfate |
| Reduced Iron | Sodium Iodate | Sodium Iodide | Sodium Tripolyphosphate |
| Sodium Sulfate | Tricalcium Phosphate | Zinc Acetate | Zinc Carbonate |
| Zinc Chloride | Zinc Oxide | Zinc Sulfate | Copper Sulfate |
| Sodium Selenite | Selenium Yeast | | |

Some examples of glucogenic precursors may include, but are not limited to, glycerol, propylene glycol, molasses, propionate, glycerine, propane diol, calcium propionate, or any combination thereof.

Some examples of antioxidants may include, but are not limited to, gallic acid, protochatechuic acid, p-coumaric acid, carnosic acid, caffeic acid, rosmarinic acid, vitamin C, vitamin E, ascorbyl palmitate, propyl gallate, resveratrol, selenium, eugenol, carvacrol, safrole, thymol, menthol, 1,8-cineole, α-terpineol, p-cymene, cinnamaldehyde, myristicin, piperine, epicatechin, quercetin, epicatechin gallate, epigallocatechin gallate, rutin, chalcone, flavone, flavanol, anthocyanin, anthocyanidin-3,5-glycoside, carnosol, rosmanol, 5-allyl (D, L) cysteine sulfoxide, diallyl sulfide, allyl trisulfide, allyl-cysteine hesperitin, naringin, neohesperidin, hesperidin, or any combination thereof.

A ruminant feed 10 may include at least one additional feed ingredient mixed with the feed. In embodiments, the at least one additional feed ingredient may include sugar beet pulp, sugar cane, wheat bran, oat hull, grain hulls, soybean hulls, peanut hulls, wood, brewery byproduct, forages, roughages, sugars, starch, cellulose, hemicellulose, wheat, corn, oats, sorghum, millet, barley, oilseed meal, soy meal, bean meal, rapeseed meal, sunflower meal, coconut meal, olive meal, linseed meal, grapeseed meal, glycogenic precursors, vitamins, minerals, amino acids, amino acid derivatives, or any combination thereof.

A feed, such as feed 10, may be configured to contain at most about five weight percent trans fatty acid. For example, the amount of trans fatty acid in the feed may be about 5 weight %, about 4 weight %, about 3 weight %, about 2 weight %, about 1 weight %, or any value or range between any two of the listed values (including endpoints). Alternatively, the feed may contain substantially no trans fatty acid. For example, substantially no trans fatty acid may be less than about 1 weight % trans fatty acid, less than about 0.5 weight % trans fatty acid, less than about 0.1 weight % trans fatty acid, or any value or range between any of the listed values (including endpoints). In an embodiment, the feed may contain no trans fatty acid.

Ruminant feeds as described herein may allow for the transfer of palmitic acid from the feed to the ruminant via the digestive tract into the blood circulation, thus improving the energy efficiency in milk production of the ruminant. When the utilization of energy becomes more effective, milk production may increase and the concentrations of protein and fat in the milk may rise. In particular, the feed may enhance fat synthesis in the mammary gland by bringing milk fat components to the cell. As such, the energy consuming synthesis in the mammary gland may not be necessary. As a result, glucose may more efficiently be used for lactose production and milk production may increase. The milk protein content may rise since there is no need to produce glucose from amino acids. In addition, the ruminant (e.g. cow) may not lose weight at the beginning of the lactation season, which may reduce fertility issues.

By feeding a feed composition that includes a nutritional component, at least one urease inhibitor, and a saturated fatty acid component to a lactating ruminant being farmed for milk production, ammonia formation may be controlled, while increasing at least one of an amount of milk produced by the lactating ruminant and a milk fat content in the milk produced by the lactating ruminant. Controlling ammonia formation may include at least one of decreasing ammonia formation in the digestive tract, slowing down ammonia formation in the digestive tract, delaying ammonia formation in the digestive tract, and decreasing ammonia formation from excrement.

In an embodiment, feeding the lactating ruminant may include feeding the lactating ruminant an animal feed comprising the nutritional component, the fatty acid component and about 10 weight percent or less urease inhibitor. The urease inhibitor may include a sulphydryl reagent, a hydroxamate, a urea analogue, or any combination thereof. Specific, non-limiting examples of urease inhibitors may include N-(n-butyl) thiophosphoric triamide, N-(n-butyl) phosphoric triamide, thiophoshoryl triamide, phenyl phosphorodiamidate, cyclohexyl thiophosphoric triamide, cyclohexyl phosphoric triamide, phosphoric triamide, hydroquinone, P-benzoquinone, hexaamidocyclotriphosphazene, thiophyridines, thiophyrimidines, thiophyridine-noxides, NN-dihalo-2-imidazolidinone, N-halo-2-oxazolidinone, acetohydroxamic acid, or any combination thereof.

In an embodiment, feeding the lactating ruminant may include feeding the lactating ruminant an animal feed comprising the nutritional component, the fatty acid component, and N-(n-butyl) thiophosphoric triamide as the urease inhibitor.

In an embodiment configured to decrease ammonia formation from excrement, the urease inhibitor may be selected or configured, for example by coating, so as to pass through the digestive tract and be excreted in the feces. If urine then contacts the feces, the urease inhibitor may inhibit urease in the feces from converting the urea in the urine into ammonia.

In an embodiment, feeding the lactating ruminant may include feeding the lactating ruminant an animal feed comprising the nutritional component, at least one urease inhibitor, and at least one fatty acid component that includes a palmitic acid moiety. As discussed previously, the palmitic acid moiety may include palmitic acid, a palmitic acid derivative, or any combination thereof. In an embodiment, the palmitic acid derivative may include palmitic acid ester, a palmitic acid sulfate, a palmitic acid phosphonate, a palmitic acid amide, a palmitic acid salt, a palmitic acid carbonate, a palmitate triglyceride, a palmitic acid carbamate, a palmitic acid imide, a palmitic acid anhydride, or any combination thereof.

As a non-limiting example configured to control ammonia formation and increase at least one of milk quality and milk production, a lactating ruminant may be fed a feed that includes at most about 10 weight percent urease inhibitor, at least about 10 weight percent free palmitic acid, and a nutritional component that includes at least one carbohydrate source, at least one protein source, at least one amino acid, at least one amino acid derivative, at least one vitamin, at least one mineral, at least one glycogenic precursor, at least one antioxidant, or any combination thereof.

In an embodiment, feeding the lactating ruminant may include feeding the lactating ruminant an animal feed comprising the nutritional component, at least one urease inhibitor, and at least one fatty acid component that includes free palmitic acid. The saturated fatty acid component may, for example, include at least about 70 weight percent free palmitic acid.

A lactating ruminant may be fed a daily amount of the feed to provide the lactating ruminant with about 0.2 kg to about 1 kg of the free palmitic acid per day. Alternatively, an average amount of milk produced per day by the lactating ruminant may be determined, and the lactating ruminant may be fed a daily amount of the feed to provide the lactating ruminant with about 5 g to about 15 g of saturated fatty acid per kg of milk produced per day. As an example, a lactating ruminant may be fed an amount of feed to provide the lactating ruminant with a daily amount of about 10 g of free palmitic acid per kg milk of produced per day.

By feeding lactating ruminants an animal feed that contains a nutritional component, at least one urease inhibitor, and at least one saturated fatty acid component, the production of milk by the ruminant may increase by at least about 1% and/or the milk fat content of the produced milk may increase by at least about 10, as compared to a similar ruminant not provided the feed.

In an embodiment as generally represented in FIG. 3, a method of producing a feed 10 for lactating ruminants may include combining 100 a nutritional component 20, at least one urease inhibitor 40, and a saturated fatty acid component 30. Any feed components, such as carbohydrate sources or nitrogen sources, for example, may be ground 102 to a pre-determined fineness, or particle size, prior to mixing 100. Smaller particles sizes may provide for improved processability during any subsequent processing steps.

For thoroughly integrating and distributing the fatty acid component 30 into the mix 10, the fatty acid component may, for example, be mixed in as a liquid or emulsion. The fatty acid component may be heated to a temperature above its melting temperature to liquefy 104 the fatty acid component. Alternatively, the fatty acid component may be dispersed in a liquid as an emulsion.

In an embodiment, the urease inhibitor 40 may be coated 106 or encapsulated with a coating material that may, for example, protect the urease inhibitor from rumen microorganisms, and/or delay the exposure of the urease inhibitor for delayed function in the digestive tract. For example, the urease inhibitor 40 may be coated with at least one of chitosan, a lipid/protein mixture, a pH-dependent polymer, and a commercial lipid formulations, such as Balchem's SHURE technology (Balchem Corp., New Hampton, N.Y.) and Innovad's NOVILYS (Innovad sa/nv, Essen, Belgium).

After mixing 100, the components may be formed into pellets 60, by any of various pelletizing methods, and, if needed, dried to a predetermined moisture content. In an embodiment, the feed mixture may be extruded 108 and portioned 110 into pellets.

In an embodiment, a method of producing a feed 10 for lactating ruminants may include combining a nutritional component 20, at least one urease inhibitor 40, and a saturated fatty acid component 30 to produce a feed that contains up to about 10 weight percent urease inhibitor and/or at least about 10 weight percent saturated fatty acid component.

As an example, a feed 10 may be produced by combining the nutritional component 20, the saturated fatty acid component 30 and a urease inhibitor 40 selected from a sulphydryl reagent, a hydroxamate, a urea analogue, or any combination thereof. As previously discussed, the urease inhibitor may be selected from N-(n-butyl) thiophosphoric triamide, N-(n-butyl) phosphoric triamide, thiophoshoryl triamide, phenyl phosphorodiamidate, cyclohexyl thiophosphoric triamide, cyclohexyl phosphoric triamide, phosphoric triamide, hydroquinone, P-benzoquinone, hexaamidocyclotriphosphazene, thiophyridines, thiophyrimidines, thiophyridine-noxides, NN-dihalo-2-imidazolidinone, N-halo-2-oxazolidinone, acetohydroxamic acid, or any combination thereof. In an embodiment, a feed may be produced by combining the nutritional component, the saturated fatty acid, and N-(n-butyl) thiophosphoric triamide as the urease inhibitor.

In a further embodiment, a method of producing a feed 10 for lactating ruminants may include combining the nutritional component 20, at least one urease inhibitor 40, and a saturated fatty acid component 30 that includes a palmitic acid moiety. The palmitic acid moiety may include palmitic acid, a palmitic acid derivative, or any combination thereof. In an embodiment, the palmitic acid derivative may include a palmitic acid ester, a palmitic acid sulfate, a palmitic acid phosphonate, a palmitic acid amide, a palmitic acid salt, a palmitic acid carbonate, a palmitate triglyceride, a palmitic acid carbamate, a palmitic acid imide, a palmitic acid anhydride, or any combination thereof. In an embodiment, the saturated fatty acid component may include at least about 70 weight percent free palmitic acid. In an alternate embodiment, the saturated fatty acid component may include at least about 90 weight percent free palmitic acid.

In a further embodiment, a method of producing a feed 10 for lactating ruminants may include combining a nutritional component 20, at least one urease inhibitor 40, and a saturated fatty acid component 30 that includes stearic acid to produce an animal feed. In an embodiment, the saturated fatty acid may include at most about 30 weight percent stearic acid.

Example 1: Ruminant Feed Composition

A feed composition for lactating ruminants will include about 20 wt % palmitic acid, 18 wt % other lipids, 35 wt % protein, 19 wt % starch, 5 wt % N-(n-butyl) thiophosphoric triamide (urease inhibitor), and 3 wt % other ingredients (vitamins, minerals, etc.).

EXAMPLES

Example 2: Method for Producing Ruminant Feed

A feed for lactating ruminants having the composition of Example 1 will be produced. In a first process, pre-determined amounts of feed grain (wheat, barley, oats), sugar beet pulp, wheat bran, molasses, protein crush (rapeseed, soya), wheat middlings, minerals, premixes (vitamins, mineral nutrients), propylene glycol, glycerol/sodium propionate, amino acid mixture, B vitamin mixture, and carnitine will be combined to form a nutritional component that contains about 24 wt % lipids, about 46 wt % protein, about 26 wt % starch, and about 4 wt % other ingredients. The ingredients will be processed and ground into particles to produce a first mixture.

Free palmitic acid will be warmed to a temperature of about 65° C. to melt the palmitic acid and form a liquid. The melted palmitic acid and N-(n-butyl) thiophosphoric triamide will be added to the first mixture to obtain the content as set forth in Example 1. The resultant mixture will be thoroughly mixed and extruded into pellets of feed.

Example 3: Two-Month Study Confirming Efficacy of Palmitic Acid/N-(n-Butyl) thiophosphoric triamide Feed A feeding experiment will be performed for about two months where a conventional complete feed will be replaced by a feed having the following composition (% by weight):

| | |
|---|---|
| Sugar beet pulp | 19 |
| Barley | 19 |

-continued

| | |
|---|---|
| Palmitic acid | 20 |
| Wheat bran | 13 |
| Oat bran | 9 |
| Propylene glycol | 9 |
| N-(n-butyl) thiophosphoric triamide | 5 |
| Molasses | 2 |
| Sodium bicarbonate | 2 |
| Biotin | 1 |
| Carnitine premix | 0.5 |
| Methionine premix | 0.5 |

The above test feed will be given to one set of cows, and a standard conventional complete feed will be given to a second set of cows as a reference. Based on the following results that were obtained for a test feed with non-covalently bonded palmitic acid in comparison to a reference feed:

| | Reference | Test feed |
|---|---|---|
| Milk kg/d | 29.5 | 32.5 |
| Fat wt % | 3.98 | 4.43 |
| Protein wt % | 3.15 | 3.37 |

Expected results for a feed with the formulation as provided above will show that the milk production as well as fat and protein concentrations increased significantly. Ammonia production within the digestive tract will be reduced, and the degree of feed utilization, measured as the efficiency of utilization of metabolizable energy intake for milk production, will significantly improve.

This disclosure is not limited to the particular systems, devices and methods described, as these may vary. The terminology used in the description is for the purpose of describing the particular versions or embodiments only, and is not intended to limit the scope.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A feed composition for lactating ruminants, the feed composition comprising:
    a nutritional component;
    a saturated fatty acid component; and
    at least one urease inhibitor, wherein at least some of the at least one urease inhibitor comprises a coating, wherein the coating is configured to protect the coated at least one urease inhibitor in the rumen to delay an exposure of the coated at least one urease inhibitor for delayed function in a digestive tract of the animal.

2. The feed composition of claim 1, wherein the feed composition comprises no more than about 10 weight percent of the at least one urease inhibitor.

3. The feed composition of claim 1, wherein the at least one urease inhibitor comprises a sulphydryl reagent, a hydroxamate, a urea analogue, or any combination thereof.

4. The feed composition of claim 1, wherein the at least one urease inhibitor comprises N-(n-butyl)thiophosphoric triamide, N-(n-butyl)phosphoric triamide, thiophoshoryl triamide, phenyl phosphorodiamidate, cyclohexyl thiophosphoric triamide, cyclohexylphosphoric triamide, phosphoric triamide, hydroquinone, p-benzoquinone, hexaamidocyclotriphosphazene, thiopyridines, thiopyrimidines, thiopyridine-n-noxides, N,N-dihalo-2-imidazolidinone, N-halo-2-oxazolidinone, acetohydroxamic acid, or any combination thereof.

5. The feed composition of claim 1, wherein the coating comprises at least one of chitosan, a lipid/protein mixture, pH-dependent polymers, commercial lipid formulations, or any combination thereof.

6. The feed composition of claim 1, wherein the feed composition comprises at least about 10 weight percent of the saturated fatty acid component.

7. The feed composition of claim 1, wherein the saturated fatty acid component comprises at least one saturated fatty acid moiety having a melting temperature of about 60° C. to about 80° C.

8. The feed composition of claim 1, wherein the saturated fatty acid component comprises palmitic acid, a palmitic acid derivative, or any combination thereof.

9. The feed composition of claim 1, wherein the saturated fatty acid component comprises a palmitic acid derivative comprising a palmitic acid ester, a palmitic acid sulfate, a palmitic acid phosphonate, a palmitic acid amide, a palmitic acid salt, a palmitic acid carbonate, a palmitate triglyceride, a palmitic acid carbamate, a palmitic acid imide, a palmitic acid anhydride, or any combination thereof.

10. The feed composition of claim 1, wherein the feed composition contains substantially no trans fatty acid.

11. The feed composition of claim 1, wherein:
    the feed composition comprises at least about 10 weight percent of the saturated fatty acid component;
    the saturated fatty acid component comprises at least about 90 weight percent of free palmitic acid;
    the feed composition contains substantially no trans fatty acid;
    the feed composition comprises equal to or less than about 10 weight percent of the at least one urease inhibitor; and
    the at least one urease inhibitor comprises N-(n-butyl) thiophosphoric triamide, cyclohexylphosphoric triamide, phenyl phosphorodiamidate, or any combination thereof.

12. The feed composition of claim 1, wherein the nutritional component comprises a carbohydrate component, a protein component, an amino acid component, a vitamin, a mineral, a glycogenic precursor, an antioxidant, or any combination thereof.

13. The feed composition of claim 1, wherein the nutritional component comprises an amino acid component comprising leucine, protected forms or derivatives of leucine, lysine, protected forms or derivatives of lysine, histidine, protected forms or derivatives of histidine, valine, protected forms or derivatives of valine, arginine, protected forms or derivatives of arginine, threonine, protected forms or derivatives of threonine, isoleucine, protected forms or derivatives of isoleucine, phenylalanine, protected forms or derivatives of phenylalanine, methionine, protected forms or derivatives of methionine, tryptophan, protected forms or derivatives of tryptophan, or any combination thereof.

14. The feed composition of claim 1, wherein the nutritional component comprises a vitamin comprising vitamin A, vitamin D, vitamin E, vitamin B1, vitamin B2, pantothenic acid, niacin, biotin, choline, or any combination thereof.

15. The feed composition of claim 1, wherein the nutritional component comprises a mineral comprising Ca, Na, Mg, P, K, Mn, Zn, Se, Cu, I, Fe, Co, Mo, or any combination thereof.

16. The feed composition of claim 1, wherein the nutritional component comprises a glucogenic precursor comprising glycerol, propylene glycol, molasses, propionate, glycerine, propane diol, calcium propionate, or any combination thereof.

17. The feed composition of claim 1, wherein the nutritional component comprises an antioxidant comprising gallic acid, protocatechuic acid, p-coumaric acid, carnosic acid, caffeic acid, rosmarinic acid, vitamin C, vitamin E, ascorbyl palmitate, propyl gallate, resveratrol, selenium, eugenol, carvacrol, safrole, thymol, menthol, 1,8-cineole, α-terpineol, p-cymene, cinnamaldehyde, myristicin, piperine, epicatechin, quercetin, epicatechin gallate, epigallocatechin gallate, rutin, chalcone, flavone, flavanol, anthocyanin, anthocyanidin-3,5-glycoside, carnosol, rosmanol, S-allyl-(D,L)-cysteine sulfoxide, diallyl sulfide, allyl trisulfide, allyl-cysteine hesperetin, naringin, neohesperidin, hesperidin, or any combination thereof.

\* \* \* \* \*